(12) United States Patent
Pelissier et al.

(10) Patent No.: US 10,674,995 B2
(45) Date of Patent: Jun. 9, 2020

(54) ULTRASOUND IMAGING INSTRUMENT VISUALIZATION

(71) Applicant: BK Medical Holding Company, Inc., Peabody, MA (US)

(72) Inventors: Laurent Pelissier, North Vancouver (CA); Kris Dickie, Vancouver (CA); Bo Zhuang, New Westminister (CA)

(73) Assignee: BK Medical Holding Company, Inc., Peabody, MA (US)

( * ) Notice: Subject to any disclaimer, the term of this patent is extended or adjusted under 35 U.S.C. 154(b) by 1139 days.

(21) Appl. No.: 14/912,620

(22) PCT Filed: Aug. 19, 2013

(86) PCT No.: PCT/IB2013/001790
§ 371 (c)(1),
(2) Date: Feb. 18, 2016

(87) PCT Pub. No.: WO2015/025183
PCT Pub. Date: Feb. 26, 2015

(65) Prior Publication Data
US 2016/0199023 A1 Jul. 14, 2016

(51) Int. Cl.
*A61B 8/08* (2006.01)
*A61B 8/00* (2006.01)
(Continued)

(52) U.S. Cl.
CPC ............ *A61B 8/0841* (2013.01); *A61B 5/061* (2013.01); *A61B 8/0833* (2013.01);
(Continued)

(58) Field of Classification Search
CPC . A61B 10/02; A61B 10/0233; A61B 17/3403; A61B 34/20; A61B 5/061;
(Continued)

(56) References Cited

U.S. PATENT DOCUMENTS 5,967,985 A * 10/1999 Hayakawa ........... A61B 8/0833
600/440
6,216,029 B1 4/2001 Paltieli
(Continued)

OTHER PUBLICATIONS

P-W. Hsu, et al., Freehand 3D Ultrasound Calibration: A Review, CUED/F-INFENG/TR 584, Dec. 2007, pp. 1-29.

*Primary Examiner* — Amanda Lauritzen Moher
(74) *Attorney, Agent, or Firm* — Anthony M. Del Zoppo, III; Daugherty & Del Zoppo Co., LPA

(57) ABSTRACT

A method includes transitioning, via a micro-processor, an ultrasound imaging system (100) running in a first mode (128), in which a first location and a first orientation of an elongate needle (106) of an instrument (102) at a surface (111) of an object (110) is determined based on a first signal from a tracking device (112) at least on the instrument, to a second different mode, in which a second location and a second orientation of the needle within the object is determined based on an ultrasound image representing the object, in response to determining the needle penetrated the surface of the object, wherein a beam steering angle with which the ultrasound image is acquired is determined based on the first location and the first orientation of the needle, and displaying the ultrasound image.

20 Claims, 4 Drawing Sheets

(51) Int. Cl.

| | |
|---|---|
| *G06T 7/00* | (2017.01) |
| *G06T 7/10* | (2017.01) |
| *G01S 7/52* | (2006.01) |
| *A61B 5/06* | (2006.01) |
| *A61B 34/20* | (2016.01) |
| *A61B 10/02* | (2006.01) |
| *A61B 17/34* | (2006.01) |
| *G01S 15/89* | (2006.01) |

(52) U.S. Cl.
CPC .......... *A61B 8/4254* (2013.01); *A61B 8/4427* (2013.01); *A61B 8/463* (2013.01); *A61B 8/467* (2013.01); *A61B 8/52* (2013.01); *A61B 8/5207* (2013.01); *A61B 8/5215* (2013.01); *A61B 8/5238* (2013.01); *A61B 8/5246* (2013.01); *A61B 8/5269* (2013.01); *A61B 8/54* (2013.01); *A61B 34/20* (2016.02); *G01S 7/52074* (2013.01); *G06T 7/0012* (2013.01); *G06T 7/0016* (2013.01); *G06T 7/10* (2017.01); *A61B 5/066* (2013.01); *A61B 8/0891* (2013.01); *A61B 8/4245* (2013.01); *A61B 8/461* (2013.01); *A61B 10/02* (2013.01); *A61B 10/0233* (2013.01); *A61B 17/3403* (2013.01); *G01S 7/52073* (2013.01); *G01S 15/899* (2013.01)

(58) Field of Classification Search
CPC ..... A61B 5/066; A61B 8/0833; A61B 8/0841; A61B 8/0891; A61B 8/4245; A61B 8/4254; A61B 8/4427; A61B 8/461; A61B 8/463; A61B 8/467; A61B 8/52; A61B 8/5207; A61B 8/5215; A61B 8/5238; A61B 8/5246; A61B 8/5269; A61B 8/54; G01S 15/899; G01S 7/52073; G01S 7/52074; G06T 7/0012; G06T 7/0016; G06T 7/10

See application file for complete search history.

(56) References Cited

U.S. PATENT DOCUMENTS

| | | |
|---|---|---|
| 6,733,458 B1 | 5/2004 | Steins |
| 8,343,054 B1 | 1/2013 | Tamura |
| 8,348,848 B1 | 1/2013 | Tamura |
| 2007/0179379 A1 | 8/2007 | Weng et al. |
| 2010/0298705 A1 | 11/2010 | Pelissier et al. |
| 2010/0298712 A1 | 11/2010 | Pelissier et al. |
| 2012/0078103 A1* | 3/2012 | Tashiro ................ A61B 8/0841 600/443 |
| 2013/0041250 A1 | 2/2013 | Pelissier et al. |
| 2013/0096430 A1* | 4/2013 | Yoshiara ............. A61B 8/0841 600/438 |

* cited by examiner

ULTRASOUND IMAGING INSTRUMENT VISUALIZATION

RELATED APPLICATION

This application is a national filing of PCT application Serial No. PCT/IB2013/001790, filed Aug. 19, 2013, published as WO2015/025183 on Feb. 26, 2015. This application claims priority to PCT application Serial No. PCT/IB2013/001790, published as WO2015/025183 on Feb. 26, 2015.

TECHNICAL FIELD

The following generally relates to ultrasound imaging and more particularly to ultrasound imaging instrument visualization.

BACKGROUND

An ultrasound imaging apparatus has included a transducer array that transmits an ultrasound beam into an examination field of view. As the beam traverses structure (e.g., of a sub-portion of an object or subject) in the field of view, sub-portions of the beam are attenuated, scattered, and/or reflected off the structure, with some of the reflections (echoes) traversing back towards the transducer array. The transducer array receives and processes the echoes, and generates one or more images of a sub-portion of the subject or object. The one or more images are visually displayed.

Ultrasound imaging has also been used to visualize an instrument disposed in or being disposed in the object or subject. For example, ultrasound imaging has been used to produce images of a needle being positioned in a subject and to verify positioning of the needle tip for a medical procedure. Unfortunately, the image quality of the needle in the images tends to be low, e.g., due to the low signal to noise ratio of the ultrasound images and speckle. Approaches to improve visualization of a needle have included beam steering and needle shaft tracking with a tracking device on the instrument.

Beam steering has included steering the beam so that the direction of the beam is perpendicular to the instrument being visualized (e.g., the shaft of a needle), which improves image quality of the instrument. However, since the position and angle of insertion of the instrument is unknown, the ultrasound beam is steered over a wide range of angles to cover multiple possible scenarios in an attempt to find a suitable angle. Unfortunately, steering the beam to cover a wide range of angles may introduce artifacts into the images, such as false enhancement on strong tissue interfaces.

With needle shaft tracking, an electro-magnetic device(s) has been affixed to a handle of the instrument or the needle tip, and the device is calibrated so that signal received by the device(s) indicates the location/angle of the device and can be used to predict the location and orientation of the needle. With the device affixed to the handle, any bending of the needle shaft introduces error between the predicted location and the actual location of the needle tip. Having the device affixed to the needle tip mitigates this error. Unfortunately, it also requires a custom-made needle, which adds cost and limits which needles can be used.

SUMMARY

Aspects of the application address the above matters, and others.

In one aspect, a method includes transitioning, via a micro-processor, an ultrasound imaging system running in a first mode, in which a first location and a first orientation of an elongate needle of an instrument at a surface of an object relative to the ultrasound imaging device is determined based on a first signal from a tracking device at least on the instrument, to a second different mode, in which a second location and a second orientation of the needle within the object is determined based on an ultrasound image representing the object, in response to determining the needle penetrated the surface of the object, wherein a beam steering angle with which the ultrasound image is acquired is determined based on the first location and the first orientation of the needle, and displaying the ultrasound image.

In another aspect, a system includes a device with a handle that supports a needle, the handle including at least one position information emitter. The system further includes an instrument position determiner that identifies a spatial position of a shaft of the needle, relative to an object, based on an output of the at least one position emitter and generates a signal indicative thereof. The system further includes an ultrasound imaging system with a transducer array and a controller that activates acquisition of an image of the object with the transducer array using a beam steering angle based on the orientation and position information of the needle which results in activation of an ultrasound beam that traverses a direction approximately perpendicular to shaft.

In another aspect, a computer readable storage medium is encoded with computer readable instructions. The computer readable instructions, when executed by a processor, causes the processor to: automatically turn on a beam steering mode of an ultrasound imaging system based on a penetration depth of a needle in an object obtained from a signal from a tracking element of an instrument carrying the needle.

Those skilled in the art will recognize still other aspects of the present application upon reading and understanding the attached description.

BRIEF DESCRIPTION OF THE DRAWINGS

The application is illustrated by way of example and not limited by the figures of the accompanying drawings, in which like references indicate similar elements and in which.

DETAILED DESCRIPTION

The following relates to visualizing an instrument disposed in or being disposed in an object or subject. In one instance, this includes determining an insertion location and angle based on position information from a tracking device affixed to the instrument and inserting the instrument in accordance therewith. Ultrasound imaging is used to track the instrument in the object or subject using a beam steering angle automatically determined based on the insertion location and the angle.

Figure 1:
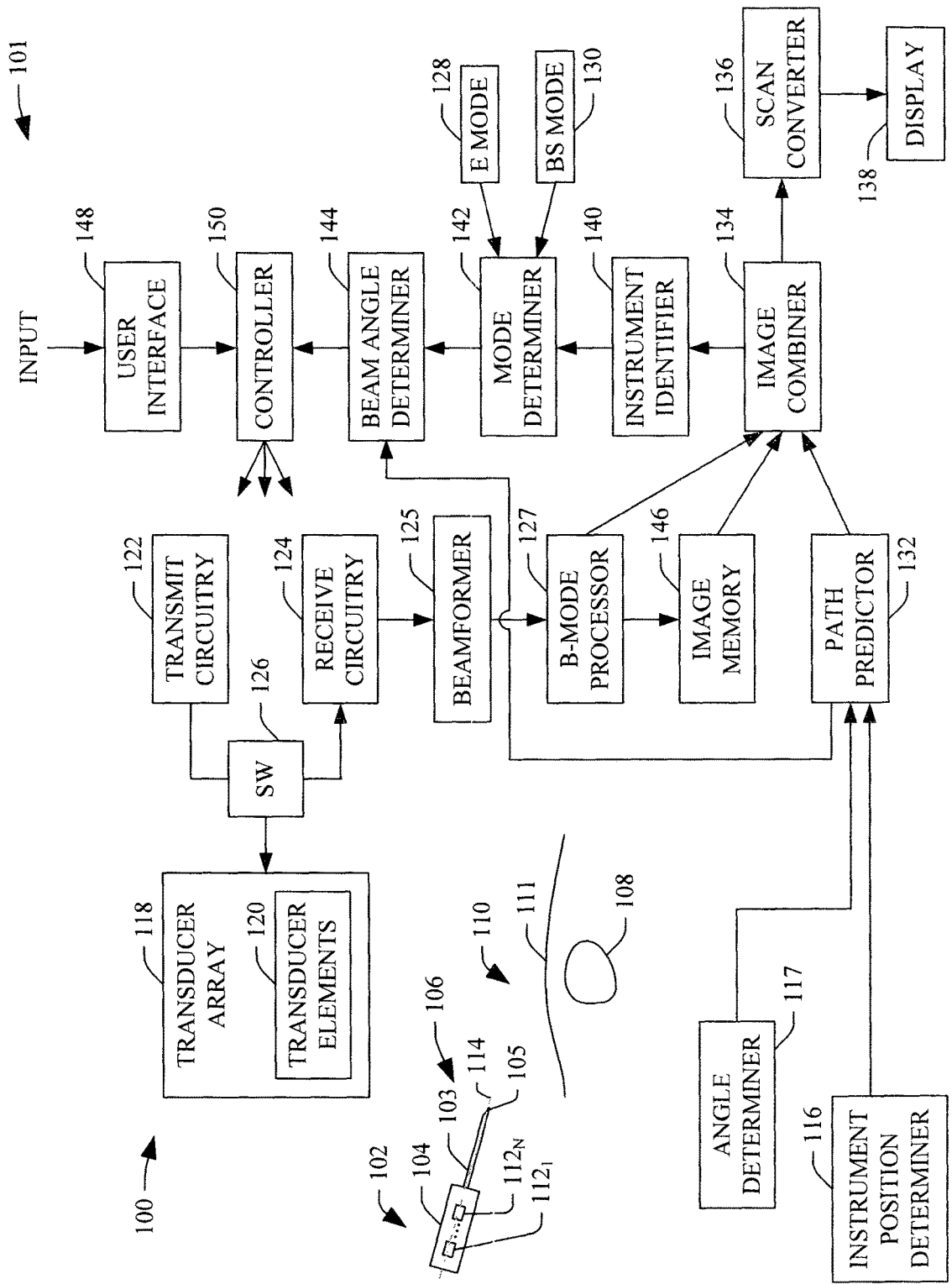
FIG. 1 schematically illustrates an imaging apparatus in connection with an instrument.

FIG. 1 schematically illustrates a system 101 including an imaging apparatus, such as an ultrasound (US) imaging apparatus 100, in connection with an instrument 102.

In the illustrated embodiment, the instrument 102 includes a handle or support 104 and an elongate needle 106 with a shaft 103 (e.g., biopsy, surgical, etc. needle), which is removably attachable to the support 104. At least a tip 105 of the needle 106, in the illustrated embodiment, is to be positioned in a sub-object 108 (e.g., a vessel, a tissue mass, etc.) of a subject or object 110 having a surface 111. In other embodiments, the instrument 102 may include another device (e.g., a guide wire, a lumen, etc.).

The support 104 includes N emitters, $112_1, \ldots, 112_N$ (collectively referred to herein as emitters 112), where N is a positive integer equal to or greater than one (1). The emitters 112 can be affixed to the support 104, as shown in FIG. 1, integrated as part of the support 104, and/or affixed to and/or integrated in the needle 106. In the illustrated example, the emitters 112 are positioned along a long axis 114 of the needle 106 and emit signals indicative of their location in three dimensional (3D) space. The signals can be processed to determine a spatial location and orientation of the emitters 112.

The determined spatial location and orientation of the emitters 112 can then be used to predict the spatial location and orientation of the needle 106. In a variation, the emitters 112 are not positioned along the long axis 114. However, the relative position of the emitters 112 to the long axis 114 is known and allows for predicting the location and orientation of the needle 106. The emitters 112 can include an electromagnetic device (e.g. with 5, 6, etc. degrees of freedom), a coil, an optical device, and/or other emitter. In an alternative embodiment, a transmitter, a passive sensor, a combination of an emitter, a transmitter and/or a passive sensor, and/or other tracking device can be affixed to the instrument 102, e.g., at the support 104 and/or the needle 106, and used to determine the spatial location and the orientation of the particular tracking device(s).

An instrument position determiner 116 detects the signals from the emitters 112 and determines the location and orientation of the emitters in 3D space based thereon. For example, where the emitters 112 include magnets, the instrument position determiner 116 can include a sensor(s) that measures a magnetic field strength of the magnets. The magnetic field strength seen at the sensor(s) depends on a distance and direction of the magnets to the sensor(s) and thus the strength and direction can be used to determine location and orientation of the emitters (and hence the needle 106). Other approaches are also contemplated herein.

Examples of suitable position determiner systems are also described in U.S. patent application Ser. No. 12/703,706, filed Feb. 10, 2010, and entitled "Ultrasound Systems Incorporating Position Sensors and Associated Method," which is incorporated herein by reference in its entirety, and U.S. patent application Ser. No. 12/775,403, filed May 6, 2010, and entitled "Freehand Ultrasound Imaging Systems and Methods for Guiding Elongate Instruments," which is incorporated herein by reference in its entirety. Other approaches are also contemplated herein. As disclosed at least in these references, an emitter, a sensor, and/or a transmitter additionally can be affixed to an ultrasound imaging system, which is described in greater detail below.

In a variation, the instrument is supported by mechanical guide, which can have a triangular or other shape configuration. The needle is fixed on one side of the triangle with a track. A sensor/emitter is attached to the needle to determine the movement of needle along the track (needs a determiner too). The angle relative to the skin surface can be determined by affixing the other side of the triangle on the skin surface. Then the angle between these two sides can be determined (either fixed or through an angle determiner). An optional angle determiner 117 would determine the angle. A distance between the needle 106 and the subject or object 110 can be fixed and pre-measured or determined Other guides and approaches are also contemplated herein.

The ultrasound imaging system 100 includes a transducer array 118 with a one or two-dimensional array of transducer elements 120. The transducer elements 120 convert electrical signals to an ultrasound pressured field and vice versa respectively to transmit ultrasound signals into a field of view and receive echo signals, generated in response to interaction with structure in the field of view, from the field of view. The transducer array 118 can be square, rectangular and otherwise shape, linear and/or curved, fully populated or sparse, etc.

Transmit circuitry 122 generates a set of pulses (or a pulsed signal) that are conveyed, via hardwire (e.g., through a cable) and/or wirelessly, to the transducer array 118. The set of pulses excites a set (i.e., a sub-set or all) of the transducer elements 120 to transmit ultrasound signals. This includes exciting the transducer array 118 to transmit signals in connection with B-mode, Doppler, and/or other imaging modes. In one instance, this includes exciting the transducer elements 120 to steer the beam based on a predetermined beam steering angle.

Figure 3A:
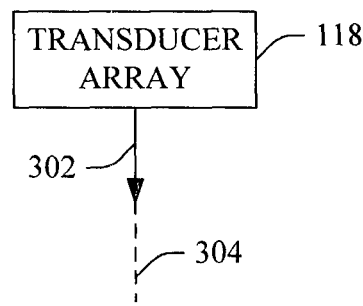
FIG. 3A illustrates a beam steering angle of zero.
Figure 3B:
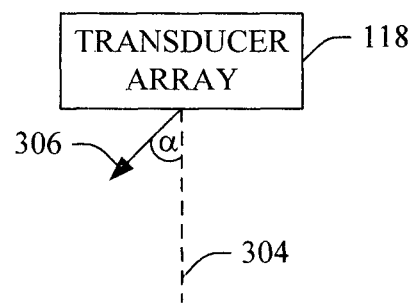
FIG. 3B illustrates a beam steering angle +20 degrees (or −20 degrees)
Figure 3C:
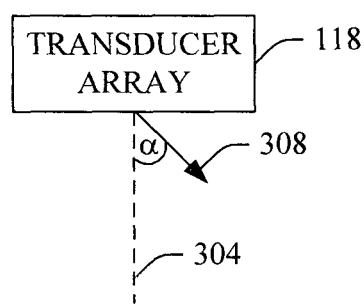
FIG. 3C illustrates a beam steering angle −20 degrees (or +20 degrees)

As utilized herein, and shown in FIG. 3A, a beam steering angle of zero (0) corresponds to an ultrasound beam 302 traversing in a direction along an axis 304 perpendicular to the transducer array 118. As utilized herein, and shown in FIG. 3B, a beam steering angle ($\alpha$) of +20 degrees corresponds to a beam 306 traversing in a direction at an angle of 20 degrees to one side of the axis 304. As utilized herein, and shown in FIG. 3C, a beam steering angle ($\alpha$) of −20 degrees corresponds to a beam 308 traversing at an angle of 20 degrees to the other side of the axis 304.

Returning to FIG. 1, receive circuitry 124 receives a set of echoes (or echo signals) generated in response to a transmitted ultrasound signal interacting with structure in the field of view. The receive circuitry 124 is configured to receive echoes corresponding at least to B-mode, Doppler, and/or other imaging. A switch (SW) 126 controls whether the transmit circuitry 122 or the receive circuitry 1124 is in electrical communication with the transducer elements 120 to transmit ultrasound signals or receive echoes.

A beamformer 125 processes the received echoes by applying time delays to echoes, weighting echoes, summing delayed and weighted echoes, and/or otherwise beamforming received echoes, creating beamformed data. The beamformer 125 and/or other processing circuitry may also perform other processing such as, but not limited to, one or more of echo-cancellation, wall-filtering, basebanding, averaging and decimating, envelope detection, log-compression, and/or other processing.

A B-mode processor 127 processes the beamformed data and generates B-mode images, which, generally, include a sequence of focused, coherent echo samples along focused scanlines of a scanplane. The B-mode images may be based on acquisitions with a beam steering angle of zero or non-zero. The B-mode processor 127 may also be configured to process the scanlines to lower speckle and/or improve specular reflector delineation via spatial compounding, and/or perform other processing such as FIR filtering, IIR filtering, edge enhancement, etc.

A path predictor 132 receives a signal from the instrument position determiner 116 and the angle determiner 117. As discussed above, the signals include the location and orientation of the emitters 112 in 3D space and the angle of the needle 106 with respect to the surface 111 of the subject or object 110. The path predictor 132, based on a mapping to the ultrasound image space, predicts a path of the needle 106 in the field of view of the transducer array 118. For example, with a straight (non-curved) needle, the predicted path may be a linear extrapolation of the line segment between the emitters 112, which, in the illustrated embodiment, is along the long axis 114 of the needle 106.

An image combiner 134 superimposes or otherwise combines indicia (e.g., a dashed line, color, etc.) representing the predicted path over the B-mode image. The image combiner 134 can also combined multiple B-mode images, as discuses herein, e.g., a B-mode image (or a sub-portion thereof) acquired with a non-zero beam steering angle with a different B-mode image (or a sub-portion thereof) acquired with a zero or different non-zero beam steering angle. The image combiner 134 can also behave as a pass through for a B-mode image.

A scan converter 136 scan converts the output of the image combiner 134 to generate data for display, e.g., by converting the data to the coordinate system of a display 138. In the illustrated embodiment, this includes scan converts a B-mode image. The scan converter 136 can be configured to employ analog and/or digital scan converting techniques. The display 138 can be a light emitting diode (LED), liquid crystal display (LCD), and/or type of display, which is part of the ultrasound imaging system 100 or in electrical communication therewith via a cable.

An instrument identifier 140 identifies the instrument 102 in the combined image that includes the predicated path superimposed over the B-mode image. This includes identifying a location of the instrument 102 with respect to the subject or object 110. For example, the instrument identifier 140 can identify whether the needle 106 is outside of, against or has penetrated the surface 111 of the subject or object 108. The instrument identifier 140 evaluates relative spatial position of the instrument 102 in conjunction with pre-calibrated data based on the needle 106 and the relative spatial position of transducer elements 120 to determine penetration of the surface 111.

A mode determiner 142 determines an operational mode of the system 100 based on the location of the needle 106 with respect to the subject or object 110. In the illustrated embodiment, the system 100 can operate in a first (emitter, or E) mode 128 in which the signal from the emitters 112 is used to track the needle 106, a second (beam steering, or BS) mode 130 in which ultrasound images are used track the needle 106, or, an optional combined mode which combines the modes 128 and 130. The latter may include a smooth transition from the mode 128 to the mode 130.

Note that as used herein the terms "first," "second," etc. in connection with mode and/or other terms in the application are used as an order of introduction of the terms herein and are not part of the naming nomenclature. As such, a term introduced as "third," for example, a "third" signal, may or may not have been generated before the "first" or "second" signal. Furthermore, even where the "third" signal is generated before the "first" or "second" signal, it still may be introduced and discussed after the "first" or "second" signal.

A beam angle determiner 144 determines a beam steering angle for the transmitted beam based on the mode. For example, when operating in the E mode 128, the beam steering angle is set to zero, with respect the axis 304, which is perpendicular to transducer array 118, or other, non-zero, beam steering angle determined based on the subject or object 110. However, when operating in the BS mode 130, the beam steering angle is determined based on the predicted location and orientation of the needle 106 with respect to the transducer array 118.

For example, in the latter instance, the beam steering angle can be set so that the beam is perpendicular or approximately perpendicular to the long axis 114 of the needle 106 and hence the needle shaft 103. Generally, the needle 106 reflects an ultrasound beam traversing at an angle closer to 90 degrees to the shaft in a manner in which the needle 106 is clearer in the generated image relative to angle less than 90 degrees. However, angles of less than 90 degrees, but around 90 degrees, are contemplated herein and may facilitate mitigating reverberation noise.

By using both, the E mode 128 and the BS mode 130, the needle 106 can be accurately tracked outside of the subject or object 110 and positioned for insertion and then accurately tracked inside the subject or object 110 through automatically setting the beam steering angle to optimize imaging the needle 106 based on the insertion location and angle and then superimposing the image of the needle 106 over an image with a beam steering angle set to optimize visualization of the subject or object 110.

The transition from the E mode 128 to the BS mode 130 may include, once the needle 106 penetrates the subject or object 110, fading away of the superimposed predicted path and visually presenting the beam steered image. The fading away can be based on a depth of the needle 106 in the object or subject 110 to mitigate error, e.g., due to bending of the needle 106. The beam steered image can be displayed alone or in combination with a previous acquired B-mode image acquired with a different beam steering angle (e.g., of zero), which can be stored in image memory 146.

A user interface (UI) 148 includes an input device(s) (e.g., a physical button, a touch screen, etc.) and/or an output device(s) (e.g., a touch screen, a display, etc.), which allow for interaction between a user and the ultrasound imaging apparatus 100. Such interaction may include activating the system 100 to use both the E mode 128 to the BS mode 130 as described herein. A controller 150 controls one or more of the components 122-148 of the system 100. Such control includes controlling one or more of these components to perform the functions described herein and/or other functions.

The US ultrasound imaging apparatus 100 can be part of a hand-held ultrasound imaging apparatus. An example of such an apparatus is described in U.S. Pat. No. 7,699,776 B2, entitled "Intuitive Ultrasonic Imaging System and Related Method thereof," filed Mar. 6, 2003, which is incorporated herein in its entirety by reference. Alternatively, the transducer array 118 is housed in a probe and the remaining components are part of a separate single computing system with an integrated and/or separate display. In this configuration, the probe and console have complementary interfaces and communicate with each other via the interfaces.

The ultrasound imaging system 100 components 128, 130, 132, 134, 136, 140, 142, and/or 144 can be implemented via one or more computer processors (e.g., a central processing unit (CPU), a microprocessor, a controller, etc.) executing one or more computer executable instructions embedded or encoded on computer readable storage medium, which excludes transitory medium, such as physical memory. However, at least one of the computer executable instructions can alternatively be carried by a carrier wave, signal, and other transitory medium and implemented via the one or more computer processors.

Figure 2:
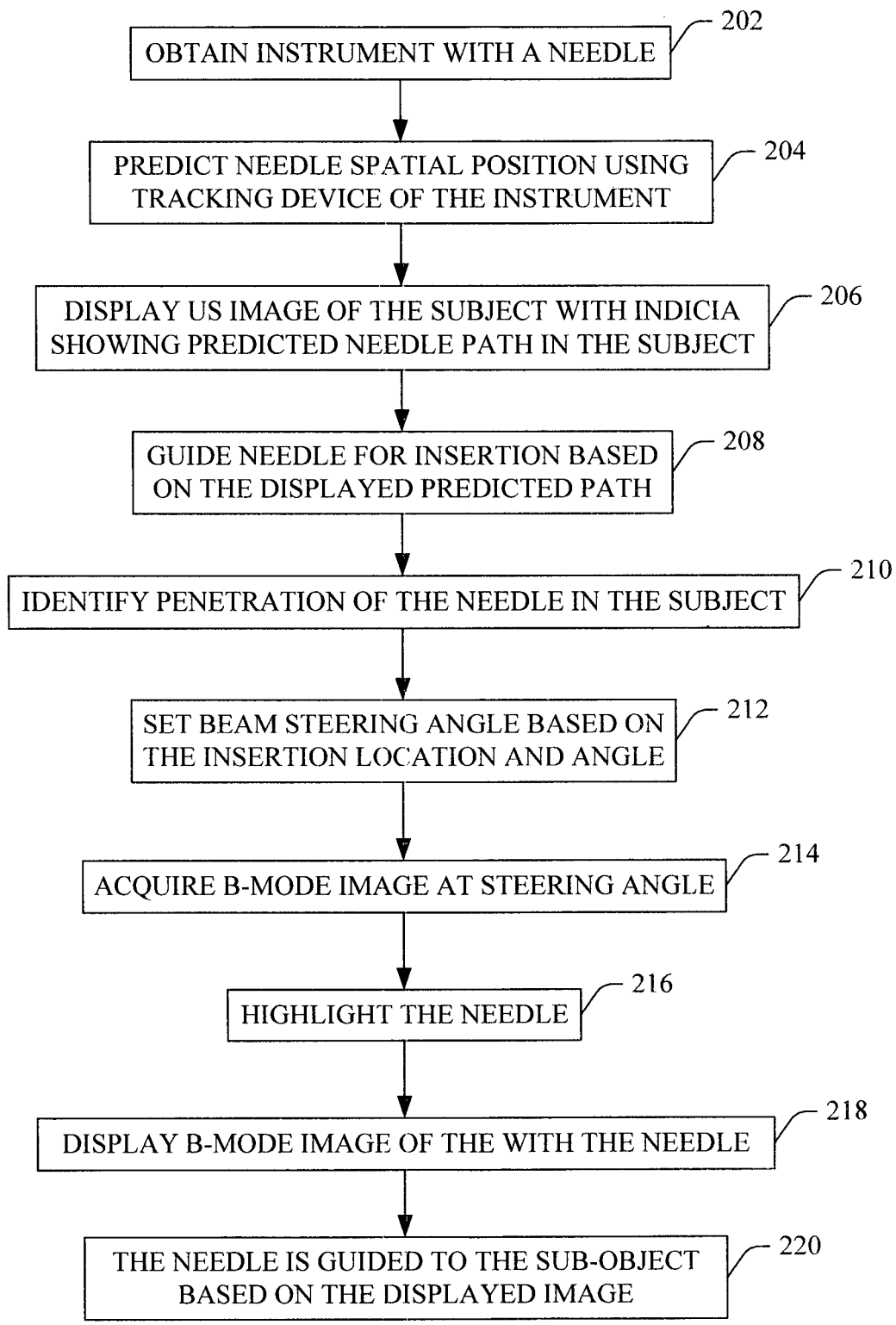
FIG. 2 illustrates an example method for guiding a needle being inserted into a subject or object.

FIG. 2 illustrates an example method for guiding a needle being inserted into a subject or object.

It is to be understood that the following acts are provided for explanatory purposes and are not limiting. As such, one or more of the acts may be omitted, one or more acts may be added, one or more acts may occur in a different order (including simultaneously with another act), etc.

At 202, the instrument 102 with the support 104 and needle 106 is obtained. Where the emitters 112 are not already attached to the instrument 102, the emitters 112 are attached to the instrument 102 and the needle position and angle are calibrated. The calibration can be done on-the-fly after the emitter 112 attachment, before-hand based on the needle type and length, and/or otherwise.

At 204, the system 100 is operated in the E mode 128 in which the signal from the emitters 112 is utilized to predict a path of the needle 106 with respect to the subject or object 110.

At 206, indicia representing the predicted path is superimposed over and displayed with a B-mode image showing the subject or object 110.

Figure 4:
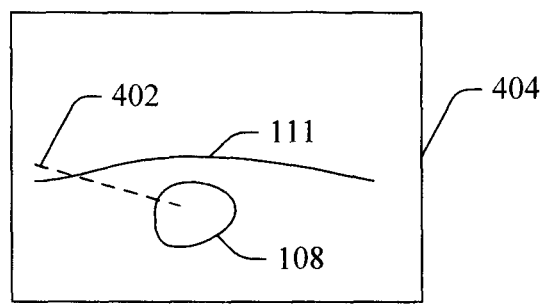
FIG. 4 illustrates an image with a predicted path of a needle of an instrument, predicted based on an emitter(s) of the instrument, superimposed over an image of a subject or object.

An example of this is shown in FIG. 4. In FIG. 4, a line 402 visually presented in a display 404 represents indicia representing a predicted path in the subject or object 110, based on a location and spatial orientation of the emitters 112 outside of the subject or object 110 and the angle of the needle 106 with respect to the surface 111 of the subject or object 110.

At 208, the predicted path is used to guide the placement (e.g., position and angle) of the needle for insertion.

Figure 5:
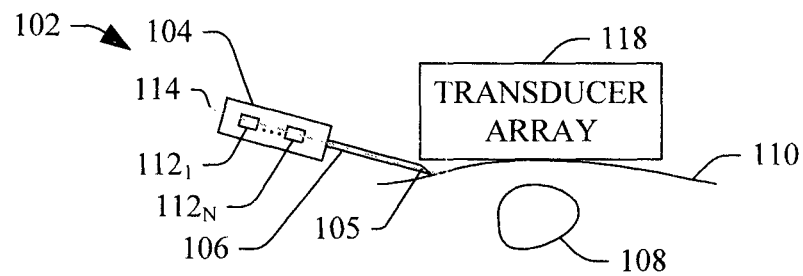
FIG. 5 illustrates placement of the needle with respect to the subject or object based on FIG. 4.

An example of this is shown in FIG. 5. In FIG. 5, the instrument 102 is positioned such that the tip 105 of the needle 106 is at a location and angle with respect to the subject or object 110. Furthermore, the transducer array 118 is shown against the subject or object 110.

At 210, penetration of the needle 106 with respect to the subject or object 110 is identified. This is achieved by evaluating the combined image.

At 212, in response thereto, the beam steering angle is automatically set based on the position and angle of the needle 106. As described herein, the beam steering angle is set to be near or approximately at 90 degrees with respect to the shaft of the needle 106.

At 214, B-mode images are acquired using the set of the beam steering angle.

At 216, the B-mode images are processed so the needle 106 is highlighted and isolated (e.g., segmented, visually enhanced, etc.) from the steered image.

At 218, the image of the needle 106 is then superimposed over a B-mode image acquired with a steering angle of zero or other steering angle based on the subject or object 110.

Figure 6:
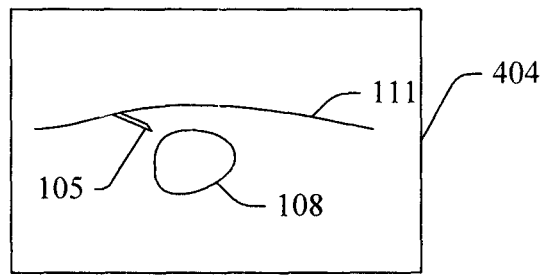
FIG. 6 illustrates an image of the needle, using beam steering angle to enhance visibility of the needle, superimposed over an image of a subject or object, acquired with a beam steering angle for the subject or object.

An example of this is shown in FIG. 6. In FIG. 6, the needle 106 is visualized in the subject or object 110 therewith.

At 220, the needle 106 is guided to the sub-object 108 using the displayed image. The displayed image is periodically updated or refreshed with a combined beam steered image and non-beam steered image, showing the current location of the needle 106.

Figure 7:
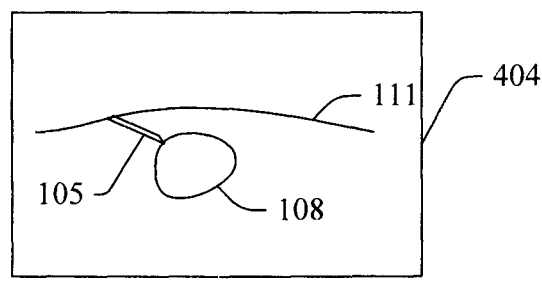
FIG. 7 illustrates an example of guiding the needle to a region of interest based on the image of FIG. 6.

An example of this is shown in FIG. 7. In FIG. 7, the needle 106 is guided to the sub-object 108 based on the visualization of FIG. 6.

As described here, the transition from determining the needle location and orientation can be based on penetration depth, which may reduce the artifact, simplify the operating process, avoid unnecessary frame rate loss, without user interaction.

With the above method, the needle 106 location can be accurately predicted, via the emitters 112, outside of the subject or object 110. Once the needle 106 penetrates the subject or object 110 and the accuracy of the prediction becomes susceptible to error, e.g., due to bending of the tip 105 of the needle 106, beam steering based on the position and angle of the needle at insertion is automatically invoked so that the needle 106 can be accurately guided within the subject or object 110.

As such, no custom-made needle with an emitter disposed at the tip is needed. In fact, all types of needle (i.e., both rigid and non-rigid) can be used with minimal to no sacrifice of artifact and/or frame rate. However, the needle path can be accurately predicted. Furthermore, the user does not have to acquire multiple images using different beam steering angles in an attempt to figure out which beam steering angle is "best" to use, via trial and error, to visualize the needle 106 within the subject or object 110. Instead, the beam steering angle is automatically set based on the emitter information.

The methods described herein may be implemented via one or more processors executing one or more computer readable instructions encoded or embodied on computer readable storage medium which causes the one or more processors to carry out the various acts and/or other functions and/or acts. Additionally or alternatively, the one or more processors can execute instructions carried by transitory medium such as a signal or carrier wave.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. A method, comprising:
    operating, via a micro-processor, an ultrasound imaging system in a first mode, including:
        receiving a first signal from a tracking device disposed on an instrument having an elongate needle that is outside of a subject at an outer surface of a sub-region of skin of a subject;
        determining a current location and a current orientation of the elongate needle of the instrument at the outer surface;
        determining a predicted path for the elongate needle to a pre-determined object in the subject from the outer surface;
        displaying an ultrasound image of an interior of the subject below the sub-region of the skin of the subject that includes the object with the predicted path superimposed over the ultrasound image;
adjusting the current location and the current orientation of the elongate needle based on the predicted path; and
detecting the elongate needle has penetrated the skin of the subject along the predicted path;
transitioning, via the micro-processor and in response to detecting the elongate needle penetrated the skin, the ultrasound imaging system from the first mode to a second different mode; and
operating, via the micro-processor, the ultrasound imaging system in the second different mode, including:
automatically determining a non-zero beam steering angle with respect to an axis perpendicular to a transducer array based on the current location and the current orientation of the elongate needle;
acquiring a first ultrasound image with the determined non-zero beam steering angle;
creating a first segmented ultrasound image of the elongated needle by segmenting the elongate needle from the first ultrasound image;
acquiring a second ultrasound image with a second beam steering angle determined based on the axis perpendicular to the transducer array;
creating a first combined ultrasound image by combining the segmented ultrasound image with the second ultrasound image; and
displaying the first combined ultrasound image.

2. The method of claim 1, wherein the automatically determined non-zero beam steering angle is perpendicular to the elongate needle.

3. The method of claim 2, wherein the second beam steering angle is zero with respect to the axis perpendicular to the transducer array.

4. The method of claim 1, wherein the second beam steering angle is non-zero with respect to the axis perpendicular to the transducer array.

5. The method of claim 1, further comprising:
guiding the elongate needle to the object based on the first combined ultrasound image.

6. The method of claim 1, further comprising:
continuing to operate the ultrasound imaging system in the second mode, including:
acquiring a third ultrasound image with the determined non-zero beam steering angle;
creating a second segmented ultrasound image of the elongated needle by segmenting the elongate needle from the third ultrasound image;
acquiring a fourth ultrasound image with the beam steering angle of zero with respect to the axis perpendicular to the transducer array;
creating a second combined ultrasound image by combining the second segmented ultrasound image with the fourth ultrasound image; and
displaying the second combined ultrasound image.

7. The method of claim 3, further comprising:
guiding the elongate needle to the object based on the first combined ultrasound image.

8. The method of claim 1, wherein the predicted path is represented as a dashed line.

9. The method of claim 1, wherein the predicted path is represented through color indicia.

10. The method of claim 1, further comprising:
detecting the elongate needle has penetrated the outer surface of the sub-region of the skin of the subject by evaluating a relative spatial position of the instrument in conjunction with pre-calibrated data based on the elongated needle and a relative spatial position of the transducer array to determine a penetration of the surface.

11. The method of claim 1, wherein the first mode is an emitter mode that tracks the elongate needle using the signal from the tracking device.

12. The method of claim 1, wherein the second mode is a beam steering mode that tracks the elongate needle using the ultrasound image.

13. The method of claim 1, wherein the tracking device includes one or more of an emitter, a transmitter, or a passive sensor.

14. The method of claim 1, further comprising:
concurrently with the transitioning, visually fading away the ultrasound image of the interior of the subject below the sub-region of the skin of the subject that includes the object with the predicted path superimposed over the ultrasound image and visually presenting the first ultrasound image determined with the non-zero beam steering angle.

15. The method of claim 14, further comprising:
fading away the ultrasound image of the interior of the subject below the sub-region of the skin of the subject that includes the object with the predicted path superimposed over the ultrasound image.

16. The method of claim 15, further comprising:
fading away the ultrasound image of the interior of the subject below the sub-region of the skin of the subject that includes the object with the predicted path superimposed over the ultrasound image based on a depth of the elongate needle in the subject.

17. The method of claim 14, further comprising:
maintaining the ultrasound image of the interior of the subject below the sub-region of the skin of the subject that includes the object with the predicted path superimposed over the ultrasound image.

18. The method of claim 1, further comprising:
displaying only first ultrasound image determined with the non-zero beam steering angle.

19. The method of claim 1, further comprising:
displaying the first ultrasound image determined with the non-zero beam steering angle with a previous acquired B-mode image acquired with a different beam steering angle.

20. The method of claim 1, further comprising:
displaying the first ultrasound image determined with the non-zero beam steering angle with a previous acquired B-mode image acquired with a different beam steering angle.

* * * * *